(12) United States Patent
Walzman (10) Patent No.: US 10,926,061 B2
(45) Date of Patent: Feb. 23, 2021

(54) BYPASS CATHETER

(71) Applicant: Daniel Ezra Walzman, Bergenfield, NJ (US)

(72) Inventor: Daniel Ezra Walzman, Bergenfield, NJ (US)

(73) Assignee: Daniel Ezra Walzman, Bergenfield, NJ (US)

( * ) Notice: Subject to any disclaimer, the term of this patent is extended or adjusted under 35 U.S.C. 154(b) by 172 days.

(21) Appl. No.: 15/932,110

(22) Filed: Feb. 5, 2018

(65) Prior Publication Data

US 2019/0217049 A1  Jul. 18, 2019

Related U.S. Application Data

(63) Continuation-in-part of application No. 15/732,953, filed on Jan. 16, 2018.

(51) Int. Cl.
*A61M 25/00* (2006.01)
*A61B 17/12* (2006.01)
(Continued)

(52) U.S. Cl.
CPC ....... *A61M 25/007* (2013.01); *A61B 17/1204* (2013.01); *A61B 17/12113* (2013.01);
(Continued)

(58) Field of Classification Search
CPC .. A61M 2025/0197; A61M 2025/1097; A61M 2025/1095; A61B 17/3207; A61B 2017/22079; A61B 2017/22084
See application file for complete search history.

(56) References Cited

U.S. PATENT DOCUMENTS 4,183,102 A   1/1980  Guiset
4,309,994 A   1/1982  Grunwald
(Continued)

FOREIGN PATENT DOCUMENTS

WO   2005112823   12/2005
WO   2012079210    6/2012

OTHER PUBLICATIONS

U.S. Appl. No. 15/258,877, filed Sep. 2016, Walzman.

*Primary Examiner* — Emily L Schmidt (57) ABSTRACT

An innovative medical device that permits rapid, minimally invasive restoration of blood flow across a vascular blockage. A system allowing for lysis or removal of said blockage. Said device creates a temporary bypass using longitudinal structure configured for insertion into the blood vessel and adapted to deliver a side hole to a target area. The side hole defines a distal first segment and a proximal second segment with a lumen to allow blood flow therethrough to at least one distal end hole. Said device includes at least one semi-permeable membrane which may act as a filter that located circumferentially around outer surface of at least one of said device segments. In an alternate embodiment, a slidable outer sheath can cover the side hole to permit reversal of blood flow from the distal end hole to a proximal end hole located outside a patient's body by means of an aspiration controller. Alternate embodiments include an optional anchoring balloon, a macerating stent or wires, perforations for fluid delivery, and a backflow valve.

23 Claims, 8 Drawing Sheets

1

(51) Int. Cl.
*A61M 25/10* (2013.01)
*A61F 2/01* (2006.01)

(52) U.S. Cl.
CPC ........... *A61F 2/013* (2013.01); *A61M 25/003* (2013.01); *A61M 25/1002* (2013.01); *A61B 2017/12054* (2013.01); *A61M 2025/0076* (2013.01); *A61M 2025/1045* (2013.01); *A61M 2025/1052* (2013.01); *A61M 2025/1095* (2013.01)

(56) References Cited

U.S. PATENT DOCUMENTS

| | | | |
|---|---|---|---|
| 4,573,966 A | 3/1986 | Weiki | |
| 4,661,094 A | 4/1987 | Simpson | |
| 4,755,176 A | 7/1988 | Patel | |
| 4,784,638 A | 11/1988 | Ghajar | |
| 4,795,427 A | 1/1989 | Helzel | |
| 4,944,745 A | 7/1990 | Sogard et al. | |
| 4,968,306 A | 11/1990 | Huss | |
| 4,970,926 A | 11/1990 | Ghajar | |
| 5,087,247 A | 2/1992 | Horn et al. | |
| 5,147,302 A | 9/1992 | Euteneuer et al. | |
| 5,163,905 A | 11/1992 | Don Michael | |
| 5,167,628 A | 12/1992 | Boyles | |
| 5,180,387 A | 1/1993 | Ghajar | |
| 5,284,473 A | 2/1994 | Calabria | |
| 5,344,402 A | 9/1994 | Crocker | |
| 5,370,617 A | 12/1994 | Sahota | |
| 5,411,479 A | 5/1995 | Bodden | |
| 5,460,610 A | 10/1995 | Don Michael | |
| 5,470,314 A | 11/1995 | Walinsky | |
| 5,542,925 A | 8/1996 | Orth | |
| 5,613,980 A | 3/1997 | Chauhan | |
| 5,639,274 A | 6/1997 | Fischell et al. | |
| 5,769,828 A | 6/1998 | Jonkman | |
| 5,800,407 A | 9/1998 | Eldor | |
| 5,830,181 A | 11/1998 | Thornton | |
| 5,840,066 A | 11/1998 | Matsuda | |
| 5,919,163 A | 7/1999 | Glickman | |
| 5,947,985 A * | 9/1999 | Imran | A61B 17/32037 604/101.05 |
| 5,951,514 A | 9/1999 | Sahota | |
| 5,954,687 A | 9/1999 | Baudino | |
| 6,013,054 A | 1/2000 | Jiun Yan | |
| 6,017,324 A | 1/2000 | Tu | |
| 6,048,333 A | 4/2000 | Lennox | |
| 6,071,285 A | 6/2000 | Lashinski | |
| 6,086,557 A | 7/2000 | Morejohn | |
| 6,129,704 A | 10/2000 | Forman et al. | |
| 6,146,370 A | 11/2000 | Barbut | |
| 6,193,685 B1 | 2/2001 | Goodin | |
| 6,223,637 B1 | 5/2001 | Hansen | |
| 6,296,655 B1 | 10/2001 | Gaudoin et al. | |
| 6,364,900 B1 | 4/2002 | Heuser | |
| 6,514,281 B1 | 2/2003 | Blaeser | |
| 8,403,911 B2 | 3/2013 | Adams et al. | |
| 8,460,240 B2 | 6/2013 | Towler | |
| 8,480,619 B2 | 7/2013 | Porter | |
| 8,496,629 B2 | 7/2013 | McKinnon | |
| 8,747,456 B2 | 6/2014 | Baim | |
| 8,951,226 B2 | 2/2015 | Hameed | |
| 8,956,383 B2 | 2/2015 | Aklog | |
| 9,295,818 B2 | 3/2016 | Riina | |
| 9,364,634 B2 | 6/2016 | Adams et al. | |
| 9,399,112 B2 | 7/2016 | Shevgoor | |
| 9,440,043 B2 | 9/2016 | Arora | |
| 9,579,494 B2 | 2/2017 | Kersten et al. | |
| 9,642,673 B2 | 5/2017 | Adams et al. | |
| 9,993,325 B2 | 6/2018 | Ren | |
| 10,299,824 B2 | 5/2019 | Walzman | |
| 10,328,246 B1 | 5/2019 | Walzman | |
| 10,314,684 B2 | 6/2019 | Walzman | |
| 10,576,245 B2 | 3/2020 | Walzman | |
| 2002/0035361 A1 | 3/2002 | Houser | |
| 2002/0052620 A1 | 5/2002 | Barbut | |
| 2002/0165572 A1 | 11/2002 | Saadat | |
| 2002/0188276 A1 * | 12/2002 | Evans | A61M 25/0021 604/509 |
| 2003/0023204 A1 | 1/2003 | Vo | |
| 2003/0198798 A1 | 10/2003 | Hehrlein | |
| 2004/0006306 A1 * | 1/2004 | Evans | A61B 17/22 604/101.03 |
| 2004/0024347 A1 | 2/2004 | Wilson | |
| 2004/0059278 A1 | 3/2004 | McPherson | |
| 2004/0122465 A1 | 6/2004 | McMurtry | |
| 2005/0038420 A1 | 2/2005 | Huybregts | |
| 2005/0171505 A1 | 8/2005 | Bertolero | |
| 2006/0235459 A1 | 10/2006 | Das | |
| 2007/0038170 A1 | 2/2007 | Joseph | |
| 2007/0185445 A1 * | 8/2007 | Nahon | A61M 25/104 604/96.01 |
| 2007/0197997 A1 | 8/2007 | Dua | |
| 2007/0225750 A1 | 9/2007 | Ren | |
| 2007/0287967 A1 | 12/2007 | Hekmat | |
| 2008/0039786 A1 * | 2/2008 | Epstein | A61B 17/12104 604/103.03 |
| 2008/0125746 A1 | 5/2008 | Shapland | |
| 2008/0281394 A1 | 11/2008 | Jones | |
| 2009/0209855 A1 * | 8/2009 | Drilling | A61M 29/00 600/435 |
| 2009/0209907 A1 | 8/2009 | Grata | |
| 2011/0190727 A1 | 8/2011 | Edmunds | |
| 2011/0245802 A1 | 10/2011 | Hayman | |
| 2011/0276023 A1 | 11/2011 | Leeflang | |
| 2012/0029436 A1 * | 2/2012 | Yassinzadeh | A61B 17/0057 604/187 |
| 2012/0116352 A1 | 5/2012 | Rangi | |
| 2012/0136242 A1 | 5/2012 | Qi | |
| 2012/0302953 A1 * | 11/2012 | Don Michael | A61B 17/22 604/101.05 |
| 2012/0316632 A1 | 12/2012 | Gao | |
| 2013/0158511 A1 * | 6/2013 | Aggerholm | A61B 17/3207 604/509 |
| 2013/0190796 A1 * | 7/2013 | Tilson | A61B 18/082 606/192 |
| 2014/0025151 A1 | 1/2014 | Gao | |
| 2014/0148751 A1 * | 5/2014 | Kassab | A61B 5/02152 604/8 |
| 2015/0127034 A1 | 5/2015 | Eaton | |
| 2015/0196303 A1 | 7/2015 | Seguin | |
| 2016/0278783 A1 | 9/2016 | Magee | |
| 2016/0324668 A1 | 11/2016 | Wallace et al. | |
| 2017/0000493 A1 * | 1/2017 | Boehm, Jr. | A61B 17/12136 |
| 2017/0007800 A1 | 1/2017 | Chao et al. | |
| 2017/0086860 A1 * | 3/2017 | Lee | A61B 17/22 |
| 2018/0126130 A1 | 5/2018 | Nitzan et al. | |
| 2018/0161552 A1 * | 6/2018 | Larson | A61M 25/1011 |
| 2018/0229010 A1 | 8/2018 | Walzman | |

\* cited by examiner

BYPASS CATHETER

CROSS REFERENCES

This is a continuation-in-part of utility application Ser. No. 15/732,953 filed Jan. 16, 2018.

BACKGROUND OF THE INVENTION

Field of the Invention

The present invention relates generally to medical device placed in a minimally invasive manner, most often percutaneous and endovascular; specifically to a bypass catheter to ameliorate ischemic injury which incorporates at least one semi-permeable membrane as a filter.

Discussion of the Prior Art

The use of devices in conjunction with medical procedures for controlling blood flow in a blood vessel is taught by the prior art. Among the most common is a balloon catheter. The balloon catheter, such as taught in the prior art, may be used to achieve isolation of a body part from its blood supply.

One of the problems associated with using balloons is that although control of the blood flow through a portion of the blood vessel is achieved, including blockage of the blood supply to a targeted site, blood flow is completely interrupted to other sites near the targeted site. The target site is the location within a vessel which requires medical intervention. The intervention may be surgical or in need of infusion of medication, typically clot-dissolving medicine.

This shortcoming can be tolerated for a short duration because when one blood vessel becomes blocked, the body normally increases the blood flow through other, essentially paralleling blood vessels. However, complex medical procedures may not be achieved during said short duration resulting in injury to said other sites or requiring multiple operations at the same targeted site. Additionally, current bypass catheters are designed to be surgically implanted, which is not practical for immediate relief of progressive ischemia caused by a sudden blockage of a blood vessel, such as from a thrombus or embolus.

The prior art teaches the use of filters generally for the purpose of trapping vascular debris. These filters are designed to stop a blood clot from traveling to the lungs causing a pulmonary embolism. A pulmonary embolism is a potentially fatal blockage in an artery that carries blood from the heart to the lungs. A blood vessel filters are also used to trap debris from migrating to other sensitive areas such as cranial vessels. Intravascular filters also have the potential to move debris and trap debris for future removal from the body, thus eliminating serious complications. Such filters take time to position and deploy, whereas time is of the essence during such interventional medical procedures to avoid complications and adverse outcomes.

Intravascular filters are generally separate medical devices from other medical devices used for surgery. There is a need to add an element to existing surgical devices to obviate the need for separate devices. This is particularly the case for neurosurgical procedures.

The present invention surmounts the problem of complete blood interruption that causes ischemia, which if not rapidly reversed will result in permanent injury.

SUMMARY OF THE INVENTION

The present invention provides an improved catheter, for use in the blood vessel system in the body. The current invention comprises a distal end hole and a side hole disposed upon the outer diameter of the device at the juncture of a first segment and second segment, and at least one filtering element. The side hole defines the end of the second segment through the proximal end hole from first segment through the distal end hole. The outer diameter of first segment and second segment are the same in some but not all embodiments.

The present invention differs structurally from the prior art as the result of the additional of least one semi-permeable membrane, such as a filter, that is positioned circumferentially outside of the first segment or second segment of the device.

The present invention combines a temporary bypass balloon, the single lumen difficult access support catheter, and the rotating irrigating and aspirating thrombectomy device. These are disclosed in Ser. No. 15/732,397 (temporary bypass balloon catheter); and Ser. Nos. 15/258,877, 15/538,898, and 15/731,478 (rotating separator, irrigator microcatheter for thrombectomy); and other Walzman single-lumen support disclosures. While Ser. No. 15/732,953 also discloses the combination of a temporary bypass balloon, the single lumen difficult access support catheter, and the rotating irrigating and aspirating thrombectomy device, the present invention teaches a structural element which is not disclosed in Ser. No. 15/732,953. Said new and additionally structural element is at least one semi-permeable membrane/filter that is circumferentially positioned outside of the end hole the first segment of the device, or end holes in branched embodiments of the current invention. The current invention is deployed to address a clot in artery or vein that is causing ischemia or heart strain because of the lack of flow through.

The present invention is capable of being positioned such that the side hole is located on one side of said artery or vein clot/blockage and the end hole of the present invention is located on the other side of the said artery or vein clot/blockage. Once the present invention is positioned, a bypass element of the present invention will allow temporary bypass of flow through the catheter, through the first segment of the catheter. More particularly, the bypass element is a segment with a side hole allowing blood to flow into said segment and out of said segment through an end hole. The side hole is located upstream from the target area. The end hole of the segment is located downstream from the target area.

In order to prevent backflow of the blood into the second segment of the catheter, the catheter would either have a valve, a smaller proximal diameter, or be attached to a pressurized fluid line, or a combination of the above. Additionally, the catheter can have a second lumen in either of the two previously described arrangements that instead of delivering fluid into a balloon, as described in the above mentioned bypass balloon invention, would deliver fluid into the clot between the side hole and the end hole. This would allow delivery of lytics or other such medications into the clot while there is an effective temporary bypass of flow through the catheter, allowing time for the directly applied medication to break up the clot and dissolve the clot while avoiding ischemic tissue injury during the interim time. Some embodiments, which have a balloon on the outer diameter as well, can comprise at least a third lumen as well.

Additionally, the present invention can have additional side loops that can macerate the clot when the catheter is rotated. Aspiration can also be applied to the catheter, which can allow aspiration through the side hole and or through the end hole. If aspiration through the end hole only is desired then the side hole can be withdrawn into a sheath so that there is no aspiration on the side hole and all aspiration forces on the end hole. Alternatively, an actively controlled valve can close said side hole.

Some embodiments can have a complex shape to the first segment, wherein rotation of the catheter itself can cause maceration. One example of such a complex shape is a sinusoidal shape (not shown).

Figure 5:
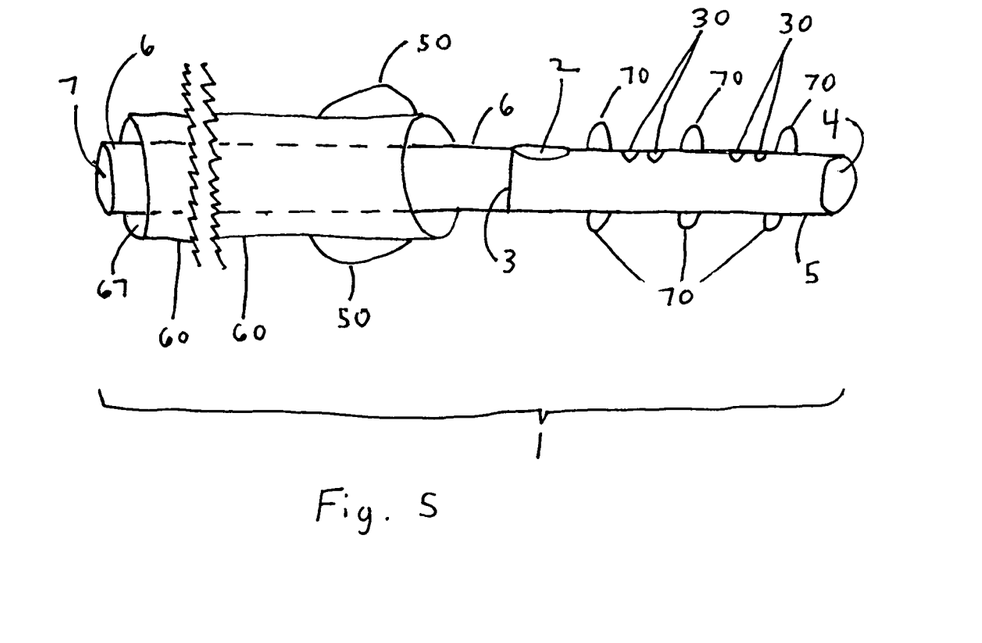
FIG. 5 depicts an alternative embodiment of the current invention.

Additionally, if there is a desire to arrest flow and or reverse flow during the maceration process to prevent downstream showering of clots, an additional optional balloon on the catheter or the sheath can be inflated, as depicted in FIG. 5.

Figure 1:
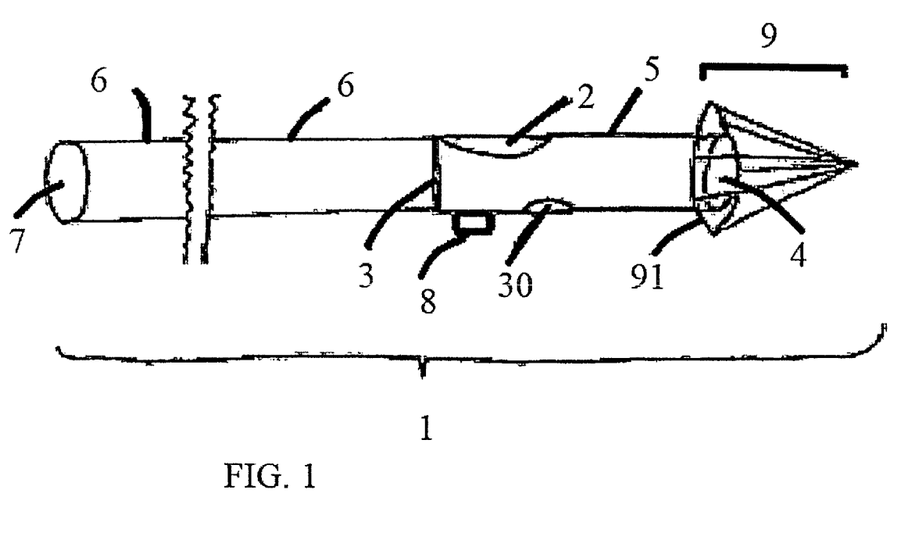
FIG. 1 is a side view of the basic embodiment of the current invention.

The present invention includes at least one semi-permeable membrane which may act as a filter that is circumferentially positioned outside of the first segment of the device, depicted by filter (9) in FIG. 1. In the preferred embodiment, said membrane is expandably umbrella-shaped having a central ring to correspond with a groove scored into the first segment, and an outer circumference that abut the vessel wall. Alternatively, the central ring may be positioned directly on the outer circumference of the first segment. Said at least one semi-permeable membrane acting as a filter can prevent emboli and capture them as the clot is broken up mechanically or dissolved with clot-busting medications. In the preferred embodiment, said at least one semi-permeable membrane is disposed circumferentially near the end hole distal to the side hole and any other structure such as macerating loops. In the preferred embodiment, said at least one semi-permeable membrane or filter is disposed within a groove about the circumference of the first segment such that said first segment may rotate within said membrane or filter. In an alternate embodiment, said membrane or filter is affixed to said first segment and rotates therewith. Affixed means said at least one semi-permeable membrane will rotate in the same direction and at the same speed as the segment it is most closely positioned. The same at least one semi-permeable membrane may be temporarily affixed to the closest segment using ultrasound, or other means such as ferrous couplers magnetized upon radiation.

In an alternate embodiment, said at least one semi-permeable membrane may be positioned circumferentially about the second segment. Said second segment is preferably grooved to correspond with the central ring of said membrane or filter, or said membrane or filter may be affixed or positioned to the outer circumference of said second segment.

Depending upon the specific procedure, the semi-permeable membrane can be both fixed or not fixed, singularly or multiply deployed=such that multiple semi-permeable membranes may be deployed about first segment and second segment, capable of being affixed or not affixed.

In an alternate embodiment, at least one semi-permeable membrane is positioned or affixed to the outer perimeter of an end hole. In alternate embodiments having more than one end hole, a semi-permeable membrane may be positioned or affixed to the perimeter of one or more such end holes.

In still another embodiment, at said least one semi-permeable membrane can be oriented in either direction depending on the direction of blood flow. The present invention is structured so as to require a single orientation with respect to the vessel into which it has been introduced. This single orientation characteristic of the present invention is a safety feature because it would not allow the present invention to be flipped resulting in the accidental misdirection of blood flow.

It should be noted that at least two versions of the present invention are possible. One where the blood flow in the vessel into which it has been introduced is flowing from the heart and the other where the blood flow in the vessel into which it has been introduced is flowing to the heart.

More specifically, each version may be structured so as to orient said least one semi-permeable membrane to intercept vessel debris (such as embolisms). One embodiment places said least one semi-permeable membrane to intercept vessel debris if the blood flow in the vessel into which it has been introduced is flowing from the heart and another embodiment places said least one semi-permeable membrane to intercept vessel debris if the blood flow in the vessel into which it has been introduced is flowing to the heart.

Additionally, for embodiments of the current invention that are capable of rotating for maceration, said least one semi-permeable membrane would be affixed to the outside of the first segment such that the filter does not rotate with the segment.

Figure 6A:
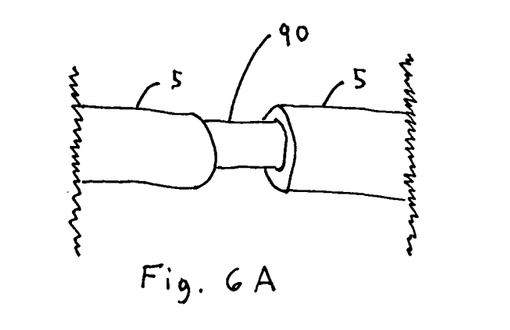
FIG. 6A depicts a segment with groove
Figure 6B:
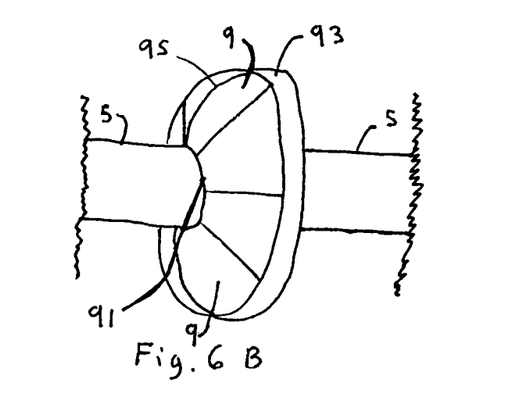
FIG. 6B depicts the segment of FIG. 6A, with a semi-permeable membrane positioned circumferentially within the groove of said segment.

For example, in preferred embodiment of the present invention as depicted in FIG. 6A, the outer surface of the first segment is scored so as to form a groove (90) in the outer surface of said first segment all the way around the outside of said first segment to which the central ring of the filter as depicted by FIG. 6B is positioned, without being actually affixed.

In this configuration said least one semi-permeable membrane would not be able to move longitudinally along the outside of the bypass catheter, because of the groove its central ring is in, but because it is not affixed to the bypass catheter if one were to rotate the bypass catheter to help macerate the clot the catheter would spin within said least one semi-permeable membrane, without the filter spinning.

The groove element of the current invention is an added safety feature as said least one semi-permeable membrane spinning can release debris or cause injury to the vessel.

Said safety feature is optional. In alternative embodiments of the present invention said least one semi-permeable membrane is actually affixed and spin. Said spinning said least one semi-permeable membrane is simpler way to design it, especially in cases where the goal is not to mechanically macerate with rotation.

The present invention may employ at least one balloon anywhere along said first segment or said second segment. Said balloon would be employed to either anchor the present invention and to restrict or stop blood blow in the vessel into which it has been introduced.

The present invention must have at least one side hole. In an alternative embodiment of the present invention at least one branching structure is incorporated into said first segment, said second segment, or both said first segment and said second segment.

Said at least one branching structure may be incorporated anywhere along said first segment or said second segment of the current invention.

In the preferred branched embodiment there are multiple first segments, with the branch occurring distal to the side hole(s), between the side hole and the distal end holes.

In the embodiment of the present invention wherein more than one branching structure is employed there will be more than one end hole.

Said at least one branching structure is not a novel feature because it is a similar configuration to the branched versions of the bypass balloon disclosed by Walzman.

Said least one branching structure is likely to be helpful for example with a clot is that a branching point. The side hole could be proximal to the clot, before the branching point, and the device could bifurcate after the side hole so that both branches could be perfused through the temporary bypass mechanism.

In the present invention, blood flows into the side hole and out one or more distal end hole(s). The present invention introduces a novel combination of either or both of two previously disclosed structures: a branching element and a filtering element. These structures can be used independently or in concert depending upon the specific medical need. In the preferred embodiment, a second segment is attached to a first segment with an optional valve located at or near the point where the distal first segment joins the second segment. A side hole is located more closely to the distal end hole, or end holes in a branched embodiment, than to the optional valve. Branching elements are located closer to the end holes than to the side hole. Semi-permeable membranes, which can take the form of umbrellas, are attached to the outside of the end hole (4) and extend from the outside of end hole (4) circumferentially until they abut the vessel wall into which the device has been inserted. The preferred embodiment also contains perforations (30) on first segment (5), including branches, which allow medication to be expelled in a target area or areas. Said perforations (30) are fed from outside the body through second segment (6) to first segment (5).

Once the present invention is properly positioned, side hole (2) will be positioned to receive blood flow from a source located upstream from a blockage, and end holes (4) positioned downstream from the target blockage, the perforations (30) positioned upstream, downstream and at the blockage. Once positioned, the present invention would allow blood to flow into the side hole (2), out of the end hole(s) (4), and allow medications introduced through second segment (6) to be delivered through perforations (30) to allow said medications to interact with the target blockage. The present invention alternatively may include a second lumen through second segment (6) which communicates from outside the patient's body through perforations (30).

There is a critical advantage to this device in that allows rapid restoration of temporary flow of blood through a blockage to avoid ischemic injury, with immediate restoration of a degree of flow beyond a clot. This will allow additional time to remove or dissolve the clot while allowing flow to the at-risk tissue. Additionally, in the case of pulmonary emboli which are large, there is an additional issue of heart strain due to the lack of outflow from the right side of the heart. The temporary bypass catheter described here can also help relieve such heart strain by allowing outflow from the right heart past said clot when there are large pulmonary emboli in the main pulmonary arteries.

BRIEF DESCRIPTION OF THE DRAWINGS

The invention will be better understood and objects other than those set forth above will become apparent when consideration is given to the following detailed description thereof. Such description makes reference to the annexed drawings+ wherein.

DETAILED DESCRIPTION OF THE INVENTION

The present invention combines elements of three prior inventions by Walzman, namely a temporary bypass catheter and balloon, a single lumen support catheter, and the rotating irrigating and aspirating thrombectomy device as well as at least one semi-permeable membrane which may act as a filter that is located and may be circumferentially positioned in a groove scored within, or to the outside of, at least one segment of the current invention.

The current invention is composed of a catheter with at least one distal end hole, at least one bypass window proximal to said end hole and at least one semi-permeable membrane which may act as a filter that located circumferentially within a groove, or around outer surface of at least one segment of the current invention. The present invention is capable of deploying said catheter across a blockage in a vessel.

The temporary balloon element, when present on the bypass catheter, is composed of a catheter with at least one distal end hole, at least one bypass window proximal to said end hole and a balloon element between said end hole and said bypass window. The present invention is capable of deploying said balloon element, before inflation, across a blockage in a vessel.

In the present invention, blood flows into the side hole and out one or more distal end hole(s). The present invention introduces a novel combination of either or both of two previously disclosed structures: a branching element and a filtering element. These structures can be used independently or in concert depending upon the specific medical need. In the preferred embodiment, a second segment (6) is attached to a first segment (5) with an optional valve (3) located at or near the point where first segment (5) joins second segment (6). A side hole (2) is located more closely to end hole or holes (4) than the optional valve (3). The branching elements are located closer to the end hole (4) than to side hole (2). Semi-permeable membranes (9), which can take the form of umbrellas, are attached to the outside of the end hole (4) and extend from the outside of end hole (4) circumferentially until they abut the vessel wall into which the device has been inserted. The preferred embodiment also contains perforations (30) on first segment (5), including branches, which allow medication to be expelled in a target area or areas. Said perforations (30) are fed from outside the body through second segment (6) to first segment (5).

Once the present invention is properly positioned, side hole (2) will be positioned to receive blood flow from a source located upstream from a blockage, and end holes (4) positioned downstream from the target blockage, the perforations (30) positioned upstream, downstream and at the blockage. Once positioned, the present invention would allow blood to flow into the side hole (2), out of the end hole(s) (4), and allow medications introduced through second segment (6) to be delivered through perforations (30) to allow said medications to interact with the target blockage. The present invention alternatively may include a second lumen through second segment (6) which communicates from outside the patient's body through perforations (30).

Referring now to FIG. 1, the current invention (1) there is a distal end hole (4) and a side hole (2) disposed upon the outer diameter of the device (1) of the current invention at the juncture of first segment (5) and second segment (6). Side hole (2) defines the end of second segment (6) through proximal end hole (7) from first segment (5) through distal end hole (4). The outer diameter of first segment (5) and second segment (6) are the same in some but not all embodiments. At least one semi-permeable membrane (9) is shown positioned on the first segment (5) between side hole (2) and balloon (8). It should be noted that membrane (9) is positioned on a segment at interface location (91). Interface location (91) may be groove (90) or the outer circumference of either first segment (5) or second segment (6).

The bypass catheter device (1) of the current invention is introduced through an incision in a patient's vessel and often directed to a target site by means of standard endovascular techniques, with the aid of wires and/or other delivery catheters, often under fluoroscopic guidance.

Returning to FIG. 1, first segment (5) is used to anchor device (1) so as to position side hole (2) at the desired location. Optionally, first segment (5) may be attached to a balloon (8) which, upon inflation, further anchors device (1) of the current invention in the desired position.

The present invention is positioned such that side hole (2) is positioned to accept blood flow from the patient and direct the blood through first segment (5) out through distal hole (4), bypassing said blood flow past a blockage. The current invention prevents backflow of blood in three ways, or any combination thereof.

FIG. 1 illustrates an embodiment employing valve (3) disposed at the juncture of second section (6) with side hole (2). In this embodiment, once the device (1) of the current invention is positioned in the desired position, valve (3) is closed by the user to prevent blood entering side hole (2) from flowing back into said second segment (6). The blood is thereby directed through first segment (5), through and out end hole (4), and allowed to perfuse the at risk tissue.

Figure 2:
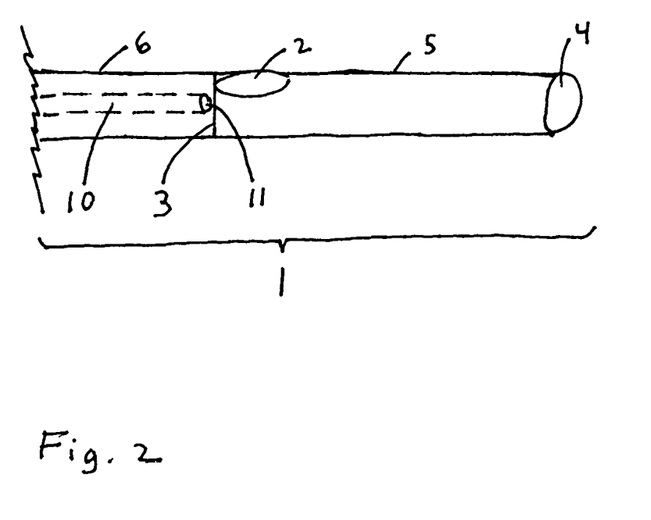
FIG. 2 is a side view of the current invention showing the inner segment with dashed lines.

In an alternative embodiment better depicted in FIG. 2, the inner diameter (10) of second segment (6) is less than the inner diameter of first segment (5). Inner diameter (10) terminates at inner hole (11). Inner hole (11) is smaller than distal end hole (4). The differential acts to constrict backflow and direct blood through first segment (5) to and out end hole (4).

In a preferred embodiment, a valve (3) and a reduced inner diameter (10) and inner hole (11) are employed to constrict backflow of blood.

Figure 3:
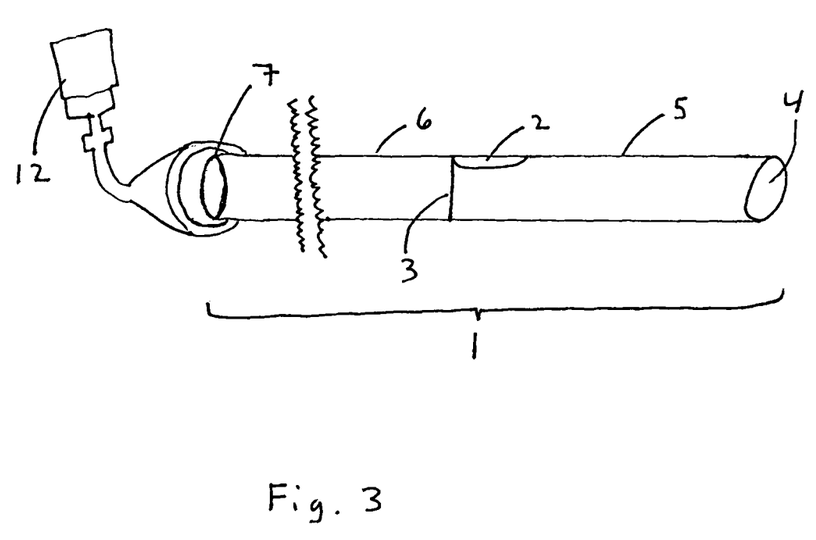
FIG. 3 depicts the first segment of the current invention connected to a pressurized fluid column.

In a still further embodiment depicted in FIG. 3, pressurized fluid may be introduced into second segment (6) to prevent the backflow of blood. FIG. 3 depicts device (1) of the current invention connected to pressurized fluid bag (12) interfacing with proximal end hole (7). Proximal end hole (7) communicates with second segment (6) through to first segment (5). Said pressurized fluid bag (12) may be connected to a flow regulator which is outside the patient's body to allow the user of the current invention to control flow of fluid through the second segment (6).

In another embodiment, pressurized fluid may be used in conjunction with valve (3) and/or inner hole (11) to prevent backflow of blood. In a still further embodiment, pressurized fluid, valve (3) and differential inner diameter (10) and inner hole (11) may be used concurrently.

Figure 4:
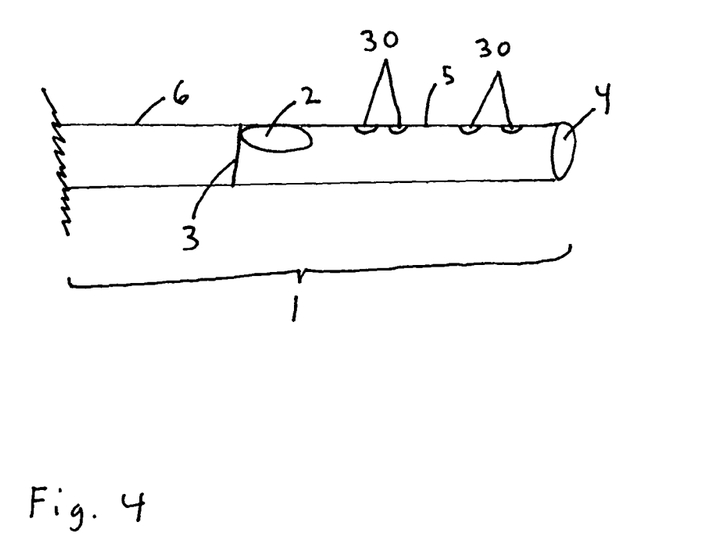
FIG. 4 is a side view of the current invention with perforations allowing infusion of medication from the proximal end.

As shown in FIG. 4, first segment (5) may optionally be perforated with at least one perforation (30). Perforations (30) are end holes for a lumen which extends from said perforations (30) and communicating with a separate irrigation channel (not shown) disposed at proximal end hole (7) and in communication with an additional controller (not shown). The fluid typically introduced into the separate channel exiting perforations (30) is designed to dissolve vessel-clogging material. For example, the fluid may be a lytic such as Alteplase, which dissolves blood clots. Said additional controller is capable of sending medication from said additional controller through communicating lumen and out perforations (30) to facilitate the irrigation of clots near first segment (5). Said medication has the capability of softening and/or changing the chemical makeup of clots proximal to perforations (30) for purposes of dislocating and/or dissolving said clot(s) or other blockage. In an alternate embodiment, the present invention device (1) is composed of co-centric lumens wherein perforations (30) communicate with the area between the internal surface of the outer lumen and the outer surface of the inner lumen, said gap extends from perforations (30) to proximal end hole (7) and communicates with said additional controller, allowing medication to be pumped from said additional controller through the area between the internal surface of the outer lumen and the outer surface of the inner lumen and out perforations (30) to allow the infusion of medication to soften, lyse, or alter the composition of clots or blockages. In the preferred embodiment, the inner channel (or area between the internal surface of the outer lumen and the outer surface of the inner lumen) terminates at the most distal perforation (30). Alternatively, the inner channel may terminate in the first segment at or near the end hole (4).

Referring now to FIG. 5, an alternate embodiment of the device (1) of the present invention further includes rotating, macerating and irrigating elements, more particularly, an slidable outer support sheath (60), macerating elements or loops (70), and/or perforations (30) used as irrigating elements. Said slidable outer support sheath (60) is capable of snugly closing side hole (2) when first segment (5) is withdrawn inside of said sheath (60). This action of withdrawing side hole (2) into outer support sheath (60) results in changing the blood-flow bypass from side hole (2) through distal end hole (4), redirecting the blood flow from distal end hole (4) out proximal end hole (7) due to an aspiration controller communicating with proximal end hole (7). Also shown in this embodiment are optional backflow valve (3) and optional anchoring balloon (50). If the operator chooses to aspirate from distal end hole (4), the bypass catheter (1) can be pulled back so that the side hole (2) is temporarily positioned within sheath (60), which is sized for a snug fit around bypass catheter (1), and aspiration force applied at proximal hole (7) will be transmitted to end hole (4), provided valve (3), when present, is open during said aspiration. It should be noted that for optimal use of this embodiment of the present invention, first segment (5) must fit snugly inside slidable outer support sheath (60).

Now referring to FIG. 6A, in the preferred embodiment of device (1) of the present invention further includes groove (90). Groove (90) is helpful for the positioning of semi-permeable membrane (9) at groove (90). Said location is referred to as interface location (91), as shown in FIG. 6B. Interface location (91) may also be located on the outside surface of a segment, and not associated with a groove. Interface location (91) may be located in multiple positions on either first segment (5) or second segment (6), or on both first segment (5) and second segment (6), depending upon the surgical procedure involved. Semi-permeable membrane (9) is shown in its expanded state with ribs (95) extending out to the circumference of outer edge (93).

Figure 6C:
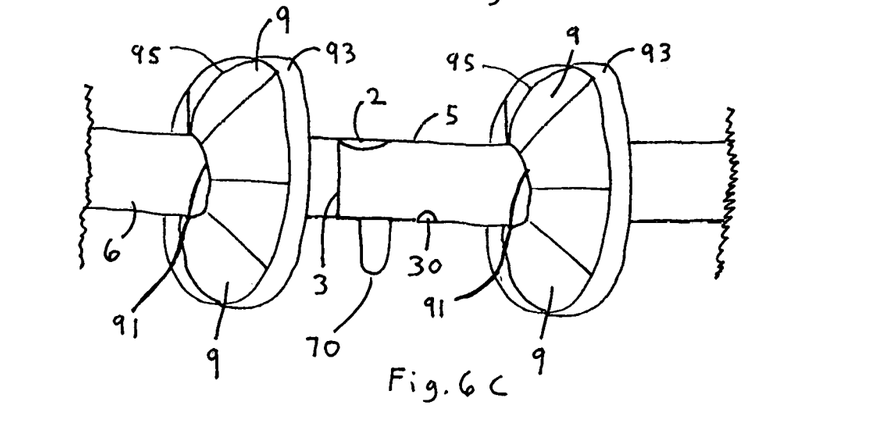
FIG. 6C depicts multiple, semi-permeable membranes positioned circumferentially within grooves scored into the first segment and second segment.

Referring now to FIG. 6C, one alternative embodiment of the present invention is shown which incorporates multiple semi-permeable membranes (9) disposed at interface locations (91), a side hole (2), a first segment (5) and second segment (6), valve (3), macerating elements or loops (70), and perforations (30) used as irrigating elements. FIG. 6C further shows membrane (9) having ribs (95), and an outer edge or circumference (93) that a radially abut a vessel wall (not shown) when deployed.

Figure 7:
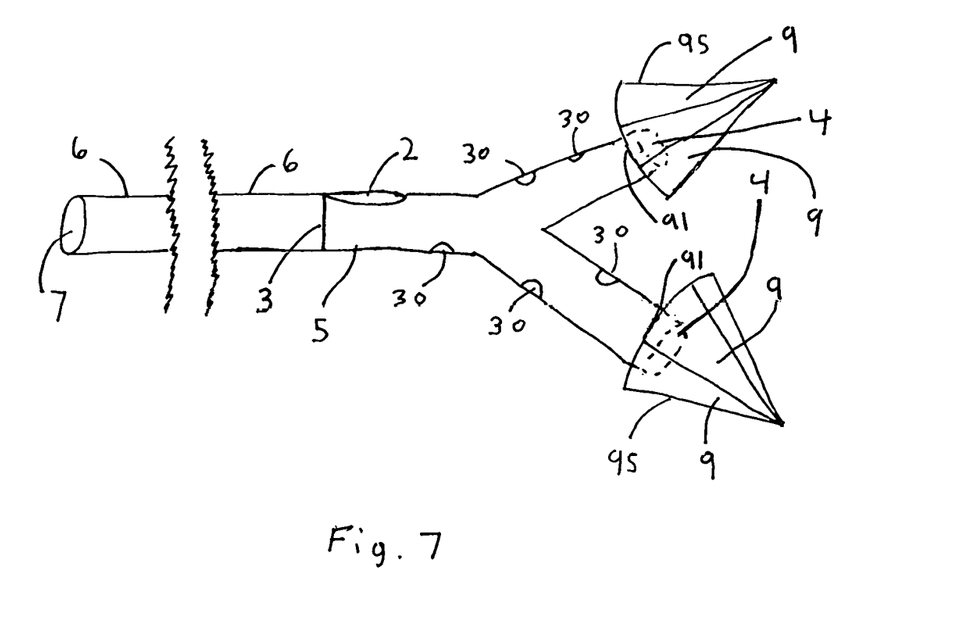
FIG. 7 depicts a side view of an embodiment of the current invention having a branched first segment, and semi-permeable membranes located at each distal end hole.

Referring now to FIG. 7, an embodiment of the current invention has a branched first segment (5) forming a Y-shape distal to side hole (2). Each branch includes perforations (30), and semi-permeable membranes (9) located at interface locations (91) at each distal end hole (4).

Figure 8A:
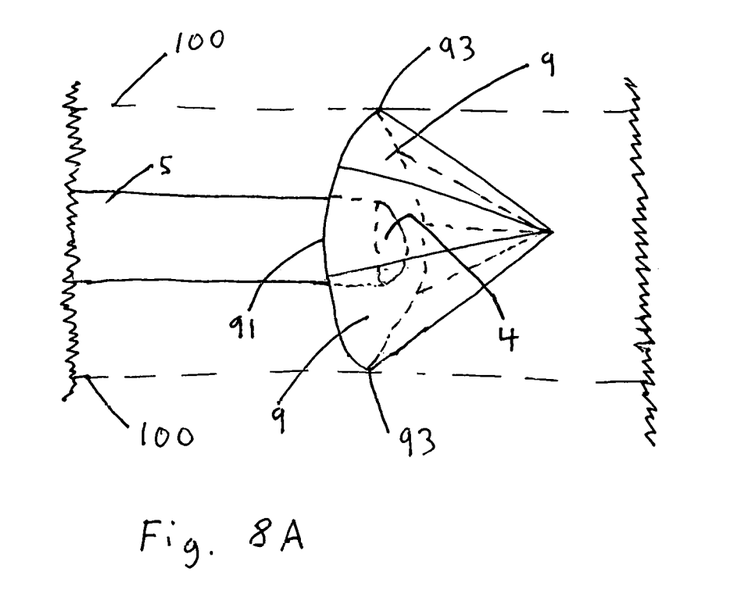
FIG. 8A is a perspective view of the semi-permeable filter of the current invention in an expanded state deployed within the vessel wall at the distal end hole.

Referring now to FIG. 8A, the semi-permeable membrane or filter (9) of the current invention in an expanded state deployed at distal end hole (4) of first segment (5). Outer edge (93) of membrane (9) abuts vessel wall (100). In the deployed state, semi-permeable membrane (9) captures emboli or debris released by the medical procedure.

Figure 8B:
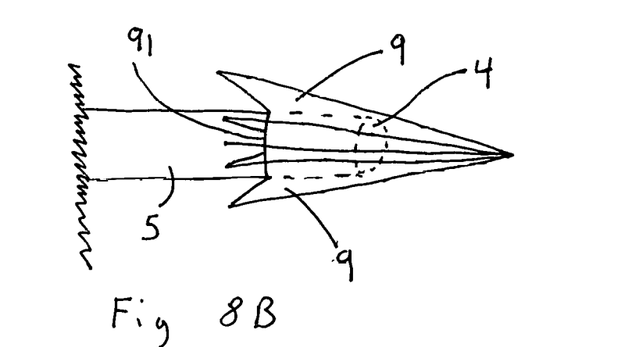
FIG. 8B is a perspective view of the semi-permeable filter of the current invention in an undeployed state positioned at the distal end hole.

Referring now to FIG. 8B shows the semi-permeable membrane or filter (9) of the current invention in an undeployed state at the distal end hole (4) of first segment (5), to facilitate insertion of device (1) through the vasculature to the desired target area. Following treatment, semi-permeable membrane (9) is retracted to this state for removal.

It will be understood that the above particular embodiments are shown and described by way of illustration only. The principles and the features of the present disclosure may be employed in various and numerous embodiments thereof without departing from the scope and spirit of the disclosure as claimed. The above-described embodiments illustrate the scope of the disclosure but do not restrict the scope of the disclosure.

What is claimed is:

1. An apparatus for bypassing a blocked vessel, comprising:
   (a) a linear longitudinal structure configured for insertion into a blood vessel,
   (b) said longitudinal structure being adapted to deliver a side hole to a location upstream of a target area,
   (c) said side hole defining a distal first segment and a proximal second segment with a lumen therethrough, wherein said side hole is perpendicular to said longitudinal structure,
   (d) said first segment having a distal end, a groove scored perpendicularly to a longitudinal axis of said longitudinal structure at said distal end, and at least one distal end hole,
   (e) said second segment having a proximal end and a proximal end hole wherein said at least one distal end hole of said first segment is in communication with said proximal end hole of said second segment;
   (f) said side hole adapted for passage of blood from upstream of said target area to said at least one distal end hole,
   (g) said first segment having no additional side holes that could allow egress of blood from said apparatus other than through the distal end hole;
   (h) an expandable umbrella-shaped semi-permeable membrane, said membrane comprising a central ring to correspond with said groove, and an outer circumference adapted to abut a vessel wall;
   (i) only a single balloon, said single balloon being disposed proximal of the membrane and between said side hole and said proximal end hole of said second segment wherein blood enters the side hole distal of the balloon; and
   (j) a valve positioned at a juncture of said first segment and said second segment prevent blood entering the side hole from flowing back into the second segment to thereby direct it through the first segment.

2. The apparatus of claim 1, wherein said valve is positioned proximally of said side hole.

3. The apparatus of claim 1, wherein said lumen defines a first diameter in said first segment a second diameter in said second segment, wherein said second diameter is less than said first diameter to prevent backflow of blood into said second segment.

4. The apparatus of claim 1, further comprising a slidable outer support sheath, wherein said first segment is snugly disposed within said slidable outer support sheath sufficiently such that said outer support sheath blocks flow through said side hole when covered.

5. The apparatus of claim 1, further comprising at least one macerating loop disposed upon said first segment distal to the single balloon, distal to said side hole and proximal to said at least one distal end hole.

6. The apparatus of claim 1, further comprising at least one branching member distal to said side hole and having a second distal end and a second distal end hole.

7. The apparatus of claim 1, wherein the semi-permeable membrane is disposed circumferentially around a non-distal outer surface of at least one of said first segment and said second segment.

8. The apparatus of claim 1, wherein said lumen constitutes a single and sole lumen extending through said longitudinal structure, said longitudinal structure including a circumferential outer wall with an inner surface circumscribing and defining said lumen.

9. The apparatus of claim 1, wherein the membrane is not affixed to the longitudinal structure such that rotation of the longitudinal structure does not rotate the membrane.

10. The apparatus of claim 1, further comprising at least one perforation disposed upon said first segment to allow injection of fluid through said apparatus from outside a patient's body.

11. The apparatus of claim 10, further comprising at least one maceration loop disposed upon said first segment distal to said side hole and proximal to said at least one distal end hole.

12. An apparatus for bypassing a blocked vessel, comprising:
   a linear longitudinal structure configured for insertion into a blood vessel,
   said longitudinal structure being adapted to deliver at least one side hole to a location upstream of a target area,
   said side hole defining a distal first segment and a proximal second segment with a lumen therethrough, wherein said side hole is perpendicular to said longitudinal structure, said at least one first segment having a distal end, a groove scored perpendicularly to a longitudinal axis of said longitudinal structure at said distal end, and at least one distal end hole, said second segment having a proximal end and a proximal end hole, said at least one side hole adapted for passage of blood from upstream of said target area to said at least one distal end hole, said first segment having no additional side holes that could allow egress of blood from said apparatus other than through the distal end hole;

an expandable umbrella-shaped semi-permeable membrane, said membrane comprising a central ring to correspond with said groove, and an outer circumference adapted to abut a vessel wall, the membrane extending around an entire circumference of the longitudinal structure; and a single balloon being disposed between a proximalmost side of the at least one side hole and said proximal end hole of said second segment.

13. The apparatus of claim 12, wherein the semi-permeable membrane is disposed circumferentially around a non-distal outer surface of at least one of said first segment and said second segment.

14. The apparatus of claim 12, wherein said apparatus is devoid of any balloons distal of said proximalmost side hole.

15. The apparatus of claim 12, wherein the membrane is not affixed to the longitudinal structure such that rotation of the longitudinal structure does not rotate the membrane.

16. The apparatus of claim 12, wherein said lumen constitutes a single and sole lumen extending through said longitudinal structure, said longitudinal structure including a circumferential outer wall with an inner surface circumscribing and defining said lumen.

17. The apparatus of claim 16, wherein said apparatus is devoid of any balloons distal of said proximalmost side hole.

18. An apparatus for bypassing a blocked vessel, comprising:
a longitudinal structure having open proximal and distal ends, the longitudinal structure being configured for insertion into a blood vessel and including:
a circumferential outer wall with an inner surface circumscribing and defining a central lumen;
a side hole formed in the circumferential outer wall and in communication with the central lumen such that blood flow is directed through the side hole, into the central lumen, and out the distal end of the longitudinal structure so as to direct blood flow around a blockage in the vessel and thereby establish a bypass; and
a circumferential groove on the longitudinal structure;
an expandable umbrella-shaped semi-permeable membrane supported on the longitudinal structure at an interface provided by the groove, wherein the membrane is not affixed to the longitudinal structure such that rotation of the longitudinal structure does not rotate the membrane; and
a single balloon disposed between the side hole and the proximal end of the longitudinal structure wherein blood enters the side hole distal of the balloon.

19. The apparatus of claim 18, wherein the apparatus is devoid of any balloons distal of the side hole.

20. The apparatus of claim 18, wherein the longitudinal structure is configured such that blood flows exclusively through the distal end of the longitudinal structure, whereby the distal end of the longitudinal structure provides a sole exit opening for blood entering the central lumen through the side hole.

21. The apparatus of claim 18, wherein the longitudinal structure includes:
a first segment;
a second segment extending from the first segment; and
a valve positioned at a juncture of the first segment and the second segment to prevent backflow of blood into the second segment.

22. The apparatus of claim 18, further comprising an outer support sheath for covering the side hole to close the side hole, the support sheath having a balloon extending therefrom.

23. The apparatus of claim 22, wherein closing of the side hole redirects blood flow proximally through the open distal end out the open proximal end.

* * * * *